US008855790B2

(12) United States Patent
Suwito et al.

(10) Patent No.: US 8,855,790 B2
(45) Date of Patent: Oct. 7, 2014

(54) SYSTEMS AND METHODS FOR LOADING A PRE-CURVED ELECTRODE ARRAY ONTO A STRAIGHTENING MEMBER

(75) Inventors: Wantjinarjo Suwito, Longmont, CO (US); Chuladatta Thenuwara, Castaic, CA (US); Chee Wui Loke, Canyon Country, CA (US); William A. Morgan, Stevenson Ranch, CA (US); Mark B. Downing, Valencia, CA (US)

(73) Assignee: Advanced Bionics AG, Staefa (CH)

(*) Notice: Subject to any disclaimer, the term of this patent is extended or adjusted under 35 U.S.C. 154(b) by 0 days.

(21) Appl. No.: 13/696,789

(22) PCT Filed: May 6, 2011

(86) PCT No.: PCT/US2011/035539
§ 371 (c)(1),
(2), (4) Date: Jan. 16, 2013

(87) PCT Pub. No.: WO2011/140452
PCT Pub. Date: Nov. 10, 2011

(65) Prior Publication Data
US 2013/0204339 A1 Aug. 8, 2013

Related U.S. Application Data

(60) Provisional application No. 61/332,491, filed on May 7, 2010.

(51) Int. Cl.
*A61N 1/04* (2006.01)
*A61N 1/05* (2006.01)
*A61B 17/34* (2006.01)
*A61B 17/00* (2006.01)
*A61N 1/36* (2006.01)

(52) U.S. Cl.
CPC ........... *A61N 1/0541* (2013.01); *A61B 17/3468* (2013.01); *A61N 1/05* (2013.01); *A61B 2017/0053* (2013.01); *A61N 1/36032* (2013.01)
USPC ........................................................ 607/137

(58) Field of Classification Search
None
See application file for complete search history.

(56) References Cited

U.S. PATENT DOCUMENTS

| 4,819,647 A | 4/1989 | Byers et al. |
| 4,898,183 A | 2/1990 | Kuzma |

(Continued)

FOREIGN PATENT DOCUMENTS

| EP | 0109304 | 5/1984 |
| EP | 1233810 | 8/2002 |

(Continued)

OTHER PUBLICATIONS

International Search Report and Written Opinion received in International Application No. PCT/US2007/083428, dated May 20, 2008.

(Continued)

*Primary Examiner* — Brian T Gedeon
*Assistant Examiner* — Ankit Tejani
(74) *Attorney, Agent, or Firm* — ALG Intellectual Property, LLC

(57) ABSTRACT

An exemplary system for loading a pre-curved electrode array onto a straightening member includes a loading tool and a straightening member. An exemplary loading tool may include a body and first and second flexible arms each having a fixed end connected to the body and a free end opposite the fixed end. The first and second flexible arms may define a straightening channel configured to constrain a pre-curved electrode array in a straightened configuration. The first and second flexible arms may be further configured to flex away from each other to receive the pre-curved electrode array into the straightening channel. The straightening member is configured to be inserted into the pre-curved electrode array while the pre-curved electrode array is in the straightened configuration and retain the pre-curved electrode array in the straightened configuration after the pre-curved electrode array is removed from the loading tool. Corresponding methods are also described.

19 Claims, 17 Drawing Sheets

(56) References Cited

U.S. PATENT DOCUMENTS

| | | |
|---|---|---|
| 5,314,411 A | 5/1994 | Bierman |
| 5,443,493 A | 8/1995 | Byers et al. |
| 5,667,514 A | 9/1997 | Heller |
| 6,070,105 A | 5/2000 | Kuzma |
| 6,125,302 A | 9/2000 | Kuzma |
| 6,129,753 A | 10/2000 | Kuzma |
| 6,149,657 A | 11/2000 | Kuzma |
| 6,195,586 B1 | 2/2001 | Kuzma |
| 6,219,580 B1 | 4/2001 | Faltys et al. |
| 6,272,382 B1 | 8/2001 | Faltys et al. |
| 6,308,101 B1 | 10/2001 | Faltys et al. |
| 6,421,569 B1 | 7/2002 | Treaba et al. |
| 6,604,283 B1 | 8/2003 | Kuzma |
| 6,968,238 B1 | 11/2005 | Kuzma |
| 7,050,858 B1 | 5/2006 | Kuzma et al. |
| 7,063,708 B2 | 6/2006 | Gibson et al. |
| 7,269,461 B2 | 9/2007 | Dadd et al. |
| 2002/0111634 A1 | 8/2002 | Stoianovici et al. |
| 2003/0093139 A1 | 5/2003 | Gibson et al. |
| 2004/0243177 A1 | 12/2004 | Svehla et al. |
| 2005/0251237 A1 | 11/2005 | Kuzma et al. |
| 2005/0267555 A1 | 12/2005 | Marnfeldt et al. |
| 2006/0058861 A1 | 3/2006 | Gibson et al. |
| 2006/0241723 A1 | 10/2006 | Dadd et al. |
| 2008/0004684 A1 | 1/2008 | Dadd et al. |
| 2008/0109011 A1 | 5/2008 | Thenuwara et al. |
| 2008/0294174 A1 | 11/2008 | Bardsley et al. |

FOREIGN PATENT DOCUMENTS

| | | |
|---|---|---|
| EP | 1341578 | 9/2003 |
| WO | WO-89/00870 | 2/1989 |
| WO | WO-93/24058 | 12/1993 |
| WO | WO-97/20530 | 6/1997 |
| WO | WO-00/71063 | 11/2000 |
| WO | WO-02/32498 | 4/2002 |
| WO | WO-0230507 | 4/2002 |
| WO | WO-02/074211 | 9/2002 |
| WO | WO-03070133 | 8/2003 |
| WO | WO-2004/012809 | 2/2004 |
| WO | WO-2008/057989 | 5/2008 |

OTHER PUBLICATIONS

Non-Final Office Action received in U.S. Appl. No. 11/933,861, dated Apr. 14, 2010.
Non-Final Office Action received in U.S. Appl. No. 11/933,861, dated Oct. 1, 2010.
Final Office Action received in U.S. Appl. No. 11/933,861, dated Apr. 28, 2011.
International Search Report and Written Opinion received in International Application No. PCT/US2011/035541, dated Oct. 7, 2011.
International Search Report and Written Opinion received in International Application No. PCT/US2011/035539, dated Dec. 29, 2011.
Non-Final Office Action received in U.S. Appl. No. 12/485,427 dated Feb. 5, 2014.
"Surgeon's Practice Kit", Instructions for Use (Part No. Z60502), *Cochlear Ltd* (ABN 96 002 618 073), 14 Mars Road, Lane Cove NSW 2066, Australia.
Non-Final Office Action received in U.S. Appl. No. 11/933,861 dated Feb. 27, 2014.

SYSTEMS AND METHODS FOR LOADING A PRE-CURVED ELECTRODE ARRAY ONTO A STRAIGHTENING MEMBER

RELATED APPLICATIONS

The present application claims priority to U.S. Provisional Patent Application No. 61/332,491 by Wantjinarjo Suwito et al., filed on May 7, 2010, and entitled "Systems and Methods for Loading a Pre-Curved Electrode Array onto a Straightening Member," the contents of which are hereby incorporated by reference in their entirety.

BACKGROUND

The natural sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers. Direct stimulation of the auditory nerve fibers leads to the perception of sound in the brain and at least partial restoration of hearing function.

To facilitate direct stimulation of the auditory nerve fibers, an electrode array may be implanted in the cochlea. Electrodes included on the electrode array form stimulation channels through which electrical stimulation pulses may be applied directly to auditory nerves within the cochlea. An audio signal may therefore be presented to a patient by translating the audio signal into electrical stimulation pulses and applying the stimulation pulses directly to auditory nerves within the cochlea via one or more of the electrodes.

The electrode array is often implanted within the scala tympani, one of three parallel ducts that make up the spiral-shaped cochlea. Electrode arrays that are implanted in the scala tympani typically include several separately connected stimulating electrode contacts longitudinally disposed on a thin, elongate, and flexible carrier. Such an electrode array is pushed into the scala tympani duct via a surgical opening made in the cochlea wall at or near the round window at the basal end of the duct.

During use, electrical current is passed into the fluids and tissues immediately surrounding the individual electrical contacts in order to create transient potential gradients that, if sufficiently strong, cause the nearby auditory nerve fibers to generate action potentials. The auditory nerve fibers arise from cell bodies located in the spiral ganglion, which lies in the bone, or modiolus, adjacent to the scala tympani on the inside wall of its spiral course. Because the density of electrical current flowing through volume conductors such as tissues and fluids tends to be highest near the electrode contact that is the source of such current, stimulation at one electrode contact site tends to selectively activate those spiral ganglion cells and their auditory nerve fibers that are closest to that contact site.

Hence, it is often desirable for the electrode contacts to be positioned as close to the ganglion cells as possible and/or to any other location (e.g., a mid-scalar location) as may serve a particular application. To this end, various pre-curved electrode arrays have been developed that have spiral-shaped resilient carriers to better conform to the shape of the scala tympani and/or other auditory structures.

A pre-curved electrode array typically has to be loaded onto a straightening member, such as a stylet, before it can be inserted into the cochlea. It may also be necessary for a surgeon to reload the pre-curved electrode array onto the straightening member during a medical procedure. However, current methods of loading and reloading pre-curved electrode arrays onto straightening members are cumbersome and often result in damage to the pre-curved electrode arrays.

SUMMARY

An exemplary system for loading a pre-curved electrode array onto a straightening member may include a loading tool and a straightening member. The loading tool may include a body, a first flexible arm having a fixed end connected to the body and a free end opposite the fixed end, and a second flexible arm having a fixed end connected to the body and a free end opposite the fixed end. The first flexible arm and the second flexible arm may define a straightening channel configured to constrain the pre-curved electrode array in a straightened configuration. The first flexible arm and the second flexible arm may also be configured to temporarily flex away from each other to receive the pre-curved electrode array into the straightening channel. The straightening member may be configured to be inserted into the pre-curved electrode array while the pre-curved electrode array is constrained within the straightening channel in the straightened configuration and retain the pre-curved electrode array in the straightened configuration after the pre-curved electrode array is removed from the straightening channel.

An exemplary method for loading a pre-curved electrode array onto a straightening member may include disposing the pre-curved electrode array in a curved configuration at least partially into a loading tool, drawing the curved portion of the pre-curved electrode array into a straightening channel of the loading tool to move the pre-curved electrode array from a curved configuration to a straightened configuration, inserting a straightening member at least partially into the pre-curved electrode array to retain the pre-curved electrode array in its straightened configuration, and removing the pre-curved electrode array and inserted straightening member from the loading tool. The loading tool of this exemplary method may include a body, a first flexible arm having a fixed end connected to the body and a free end opposite the fixed end, a second flexible arm having a fixed end connected to the body and a free end opposite the fixed end. The first flexible arm and the second flexible arm may define a straightening channel configured to constrain the pre-curved electrode array in a straightened configuration and the first flexible arm and the second flexible arm may be configured to flex away from each other to receive the pre-curved electrode array into the straightening channel.

An exemplary tool for loading a pre-curved electrode array onto a straightening member may include a body, a first flexible arm having a fixed end connected to the body and a free end opposite the fixed end, and a second flexible arm having a fixed end connected to the body and a free end opposite the fixed end. The first flexible arm and the second flexible arm define a straightening channel configured to constrain the pre-curved electrode array in a straightened configuration. The first flexible arm and the second flexible arm may also be configured to flex away from each other to receive the pre-curved electrode array into the straightening channel.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers may designate similar, but not necessarily identical, elements.

DETAILED DESCRIPTION

Exemplary systems and methods for loading a pre-curved electrode array onto a straightening member are disclosed herein. The exemplary systems and methods described herein may allow a user (e.g., a surgeon) to more efficiently and easily load a pre-curved electrode array onto a straightening member (e.g., a stylet). As a result, the user may be able to load and/or reload a pre-curved electrode array onto a straightening member as needed during a medical procedure without significantly delaying the completion of the medical procedure or damaging the electrode array.

In some examples, an exemplary system according to principles described herein may include a loading tool and a straightening member. The loading tool may include a body, a first flexible arm, and a second flexible arm. In certain examples, the first flexible arm may have a fixed end connected to the body and a free end opposite the fixed end. In a similar manner, the second flexible arm may have a fixed end connected to the body and a free end opposite the fixed end. As will be described in more detail below, the first flexible arm and the second flexible arm may define a straightening channel configured to constrain a pre-curved electrode array in a straightened configuration to facilitate the insertion of a straightening member into the pre-curved electrode array. The first flexible arm and the second flexible arm may also be configured to flex as necessary to receive the pre-curved electrode array into the straightening channel. The straightening member may be configured to be inserted into the pre-curved electrode array while constrained in the straightened configuration and retain the pre-curved electrode array in the straightened configuration after removal from the loading tool.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
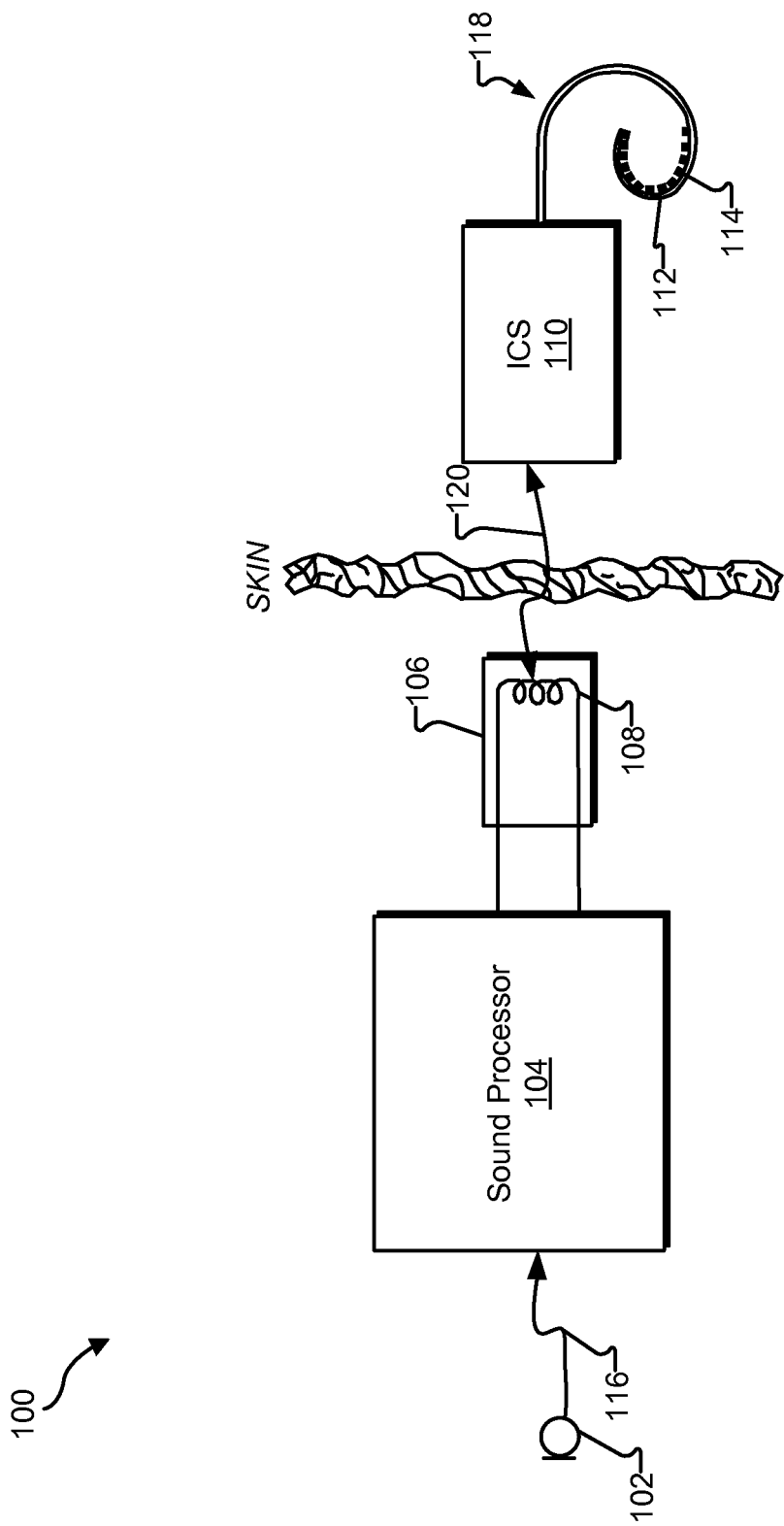
FIG. 1 illustrates an exemplary cochlear implant system according to principles described herein.

FIG. 1 illustrates an exemplary cochlear implant system 100. Cochlear implant system 100 may include a microphone 102, a sound processor 104, a headpiece 106 having a coil 108 disposed therein, an implantable cochlear stimulator ("ICS") 110, and a lead 118 having a pre-curved electrode array 112 (or simply "electrode array 112") comprising a plurality of electrodes 114. Additional or alternative components may be included within cochlear implant system 100 as may serve a particular application.

As shown in FIG. 1, microphone 102, sound processor 104, and headpiece 106 may be located external to a cochlear implant patient. In some alternative examples, microphone 102 and/or sound processor 104 may be implanted within the patient. In such configurations, the need for headpiece 106 may be obviated.

Microphone 102 may detect an audio signal and convert the detected signal to a corresponding electrical signal. The electrical signal may be sent from microphone 102 to sound processor 104 via a communication link 116, which may include a telemetry link, a wire, and/or any other suitable communication link.

Sound processor 104 is configured to direct implantable cochlear stimulator 110 to generate and apply electrical stimulation (also referred to herein as "stimulation current") to one or more stimulation sites within a cochlea of the patient. To this end, sound processor 104 may process the audio signal detected by microphone 102 in accordance with a selected sound processing strategy to generate appropriate stimulation parameters for controlling implantable cochlear stimulator 110. Sound processor 104 may include or be implemented within a behind-the-ear ("BTE") unit, a portable speech processor ("PSP"), and/or any other sound processing unit as may serve a particular application. Exemplary components of sound processor 104 will be described in more detail below.

Sound processor 104 may be configured to transcutaneously transmit one or more control parameters and/or one or more power signals to implantable cochlear stimulator 110 with coil 108 by way of communication link 120. These control parameters may be configured to specify one or more stimulation parameters, operating parameters, and/or any other parameter as may serve a particular application. Exemplary control parameters include, but are not limited to, volume control parameters, program selection parameters, operational state parameters (e.g., parameters that turn a sound processor and/or an implantable cochlear stimulator on or off), audio input source selection parameters, fitting parameters, noise reduction parameters, microphone sensitivity parameters, microphone direction parameters, pitch parameters, timbre parameters, sound quality parameters, most comfortable current levels ("M levels"), threshold current levels, channel acoustic gain parameters, front and back-end dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters. Sound processor 104 may also be configured to operate in accordance with one or more of the control parameters.

As shown in FIG. 1, coil 108 may be housed within headpiece 106, which may be affixed to a patient's head and positioned such that coil 108 is communicatively coupled to a corresponding coil included within implantable cochlear stimulator 110. In this manner, control parameters and power signals may be wirelessly transmitted between sound processor 104 and implantable cochlear stimulator 110 via communication link 120. It will be understood that data communication link 120 may include a bi-directional communication link and/or one or more dedicated uni-directional communication links. In some alternative embodiments, sound processor 104 and implantable cochlear stimulator 110 may be directly connected with one or more wires or the like.

Implantable cochlear stimulator 110 may be configured to generate electrical stimulation representative of an audio signal detected by microphone 102 in accordance with one or more stimulation parameters transmitted thereto by sound processor 104. Implantable cochlear stimulator 110 may be further configured to apply the electrical stimulation to one or more stimulation sites within the cochlea via one or more electrodes 114 of electrode array 112 of lead 118.

To facilitate application of the electrical stimulation generated by implantable cochlear stimulator 110, electrode array 112 may be inserted within a duct of the cochlea such that electrodes 114 are in communication with one or more stimulation sites within the cochlea. As used herein, the term "in communication with" refers to electrodes 114 being adjacent to, in the general vicinity of, in close proximity to, directly next to, or directly on the stimulation site. Electrode array 112 may comprise any number of electrodes 114 (e.g., sixteen) as may serve a particular application.

Figure 2:
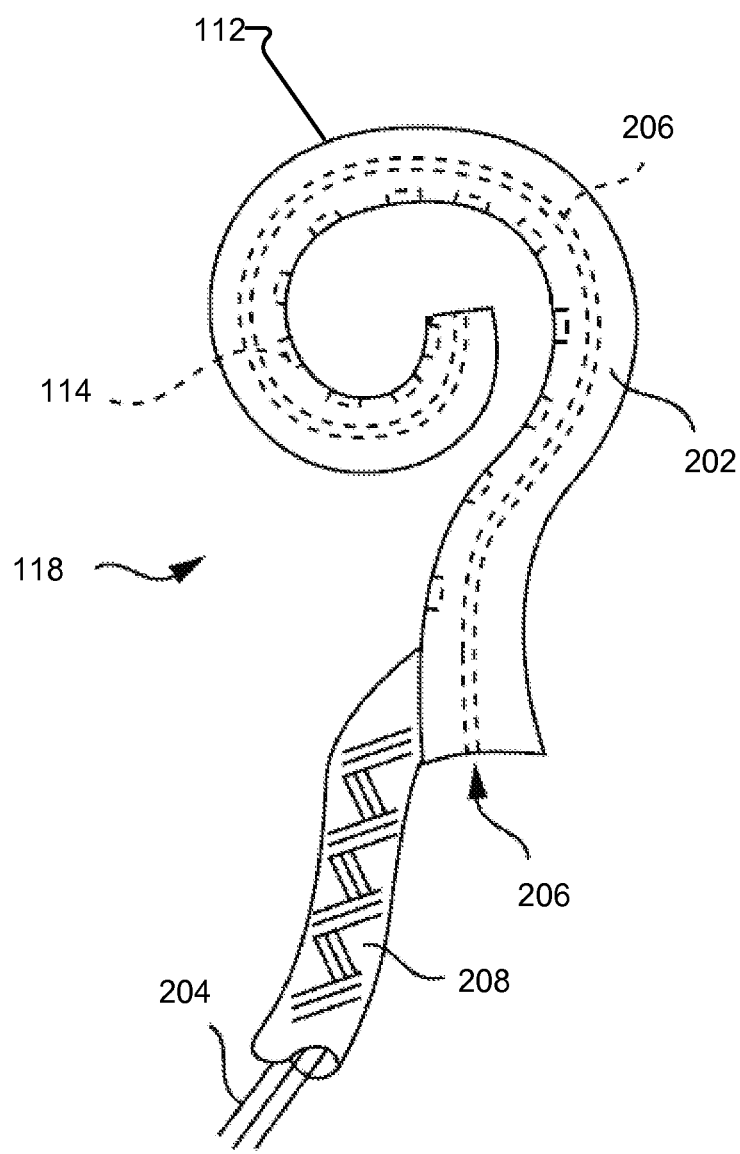
FIG. 2 illustrates an exemplary pre-curved electrode array according to principles described herein.

To facilitate proper positioning of electrodes 114, lead 118 is provided with a pre-curved electrode array 112 as shown in FIG. 2. The electrode array 112 may be substantially as shown and described in U.S. Pat. No. 4,819,647; 6,129,753; or 6,604,283, each of which is incorporated herein by reference in its respective entirety.

As shown in FIG. 2, electrode array 112 may have the same general curvature as that of a human cochlea. In some examples, electrode array 112 includes an array of electrodes 114 (also referred to as "electrode contacts 114") disposed on an elongate flexible carrier 202 and connected to corresponding wires 204, which may be insulated in some embodiments. Elongate flexible carrier 202 may be made out of any suitable material such as, but not limited to, silicone rubber or plastic, and has a hole or lumen 206 passing at least partially therethrough. In some examples, carrier 202 is constructed so as to have a built-in bias or memory force which forces carrier 202 to naturally assume the curved configuration shown in FIG. 2. In addition, the material of the carrier 202 may be configured to allow carrier 202 to be straightened when loaded on a straightening member. Hence, references made herein to "straightening a pre-curved electrode array" and/or "moving a pre-curved electrode array from a curved configuration to a straightened configuration" refer to a straightening of carrier 202. Once inserted within the duct of a cochlea, the memory force of carrier 202 forces carrier 202 to return to the desired curvature (e.g., as shown in FIG. 2).

As shown in FIG. 2, a proximal end of carrier 202 is coupled to a lead body 208 through which wires 204 continue and connect to implantable cochlear stimulator 110. Implantable cochlear stimulator 110 is thus able to make electrical connection with each of the electrodes 114 through one or more of wires 204. In some examples, the electrodes 114 of electrode array 112 are configured to be positioned along a medial electrode wall, i.e., the inside curve of carrier 202 such that they face the modiolus when implanted in the cochlea.

Figure 3:
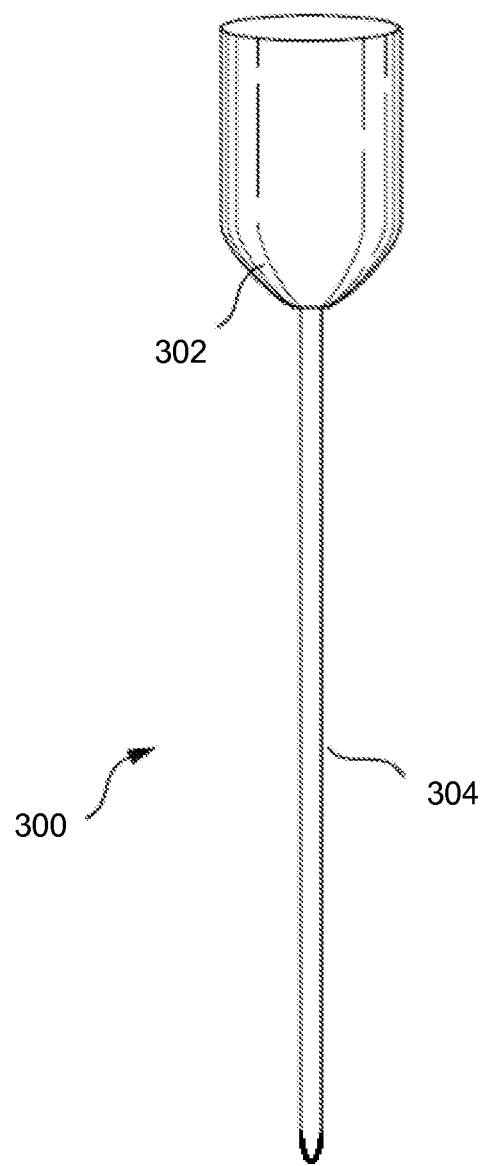
FIG. 3 is a perspective view of an exemplary straightening member that may be used to insert a pre-curved electrode array into a duct of the cochlea according to principles described herein.

As mentioned, pre-curved electrode array 112 may be loaded onto a straightening member before it can be implanted within a duct of the cochlea. FIG. 3 is a perspective view of an exemplary straightening member 300 that may be used in accordance with the systems and methods described herein. As shown in FIG. 3, straightening member 300 may include a handle member 302 coupled to a substantially straight member 304. Handle member 302 may be of a dimension to accommodate manual handling thereof and/or attachment of forceps or other tools thereto. Substantially straight member 304, as will be described in more detail below, may be configured to be at least partially inserted into a lumen of pre-curved electrode array 112. As shown, straightening member 300 may have a substantially rounded distal tip to facilitate insertion into an electrode array. In additional or alternative examples, the distal tip may have any other configuration (e.g., a bullet-shaped configuration or a substantially conical configuration) suitable for insertion into an electrode array without damaging the electrode array.

Straightening member 300 shown in FIG. 3 is a stand-alone stylet for illustrative purposes only. It will be recognized that straightening member 300 may alternatively be coupled to or a part of an insertion tool.

Straightening member 300 may be made out of any suitable material with sufficient stiffness so as to facilitate entry into the cochlea. For example, straightening member 300 may be made out of a metal, a metal alloy, a hard plastic, or any other suitable material.

Figure 4:
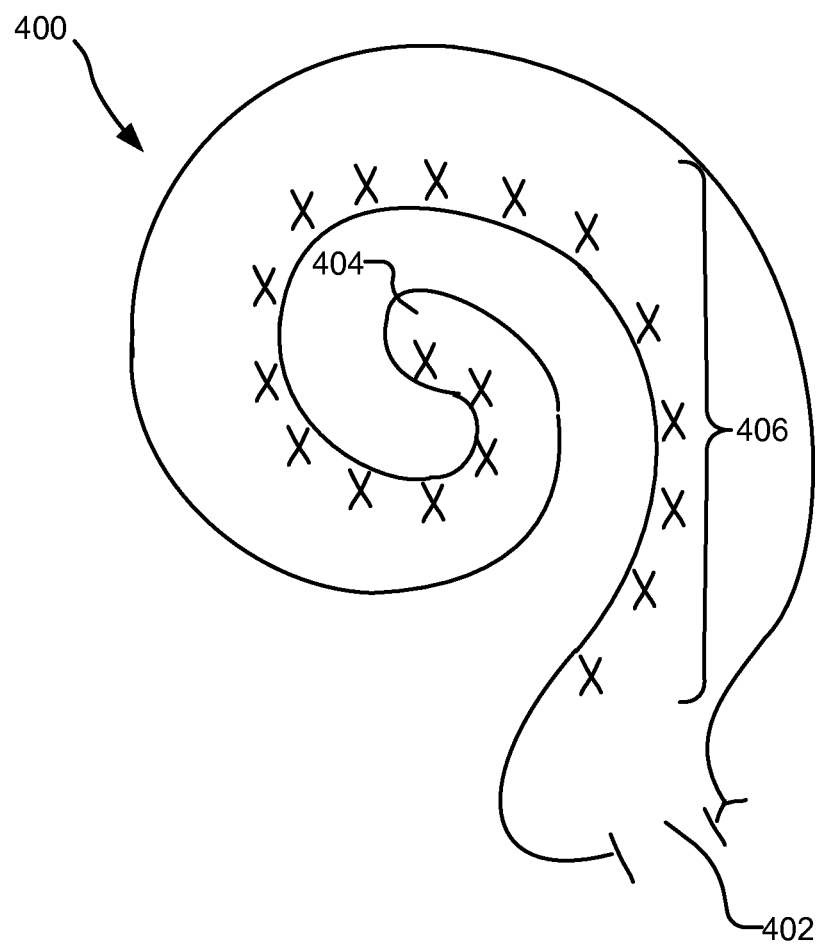
FIG. 4 illustrates a schematic structure of a human cochlea.

FIG. 4 illustrates a schematic structure of the human cochlea 400 into which electrode array 112 may be inserted. As shown in FIG. 4, the cochlea 400 is in the shape of a spiral beginning at a base 402 and ending at an apex 404. Within the cochlea 400 resides auditory nerve tissue 406, which is denoted by Xs in FIG. 4. The auditory nerve tissue 406 is organized within the cochlea 400 in a tonotopic manner. Low frequencies are encoded at the apex 404 of the cochlea 400 while high frequencies are encoded at the base 402. Hence, each location along the length of the cochlea 400 corresponds to a different perceived frequency. System 100 may therefore be configured to apply electrical stimulation to different locations within the cochlea 400 (e.g., different locations along the auditory nerve tissue 406) to provide a sensation of hearing.

Figure 5:
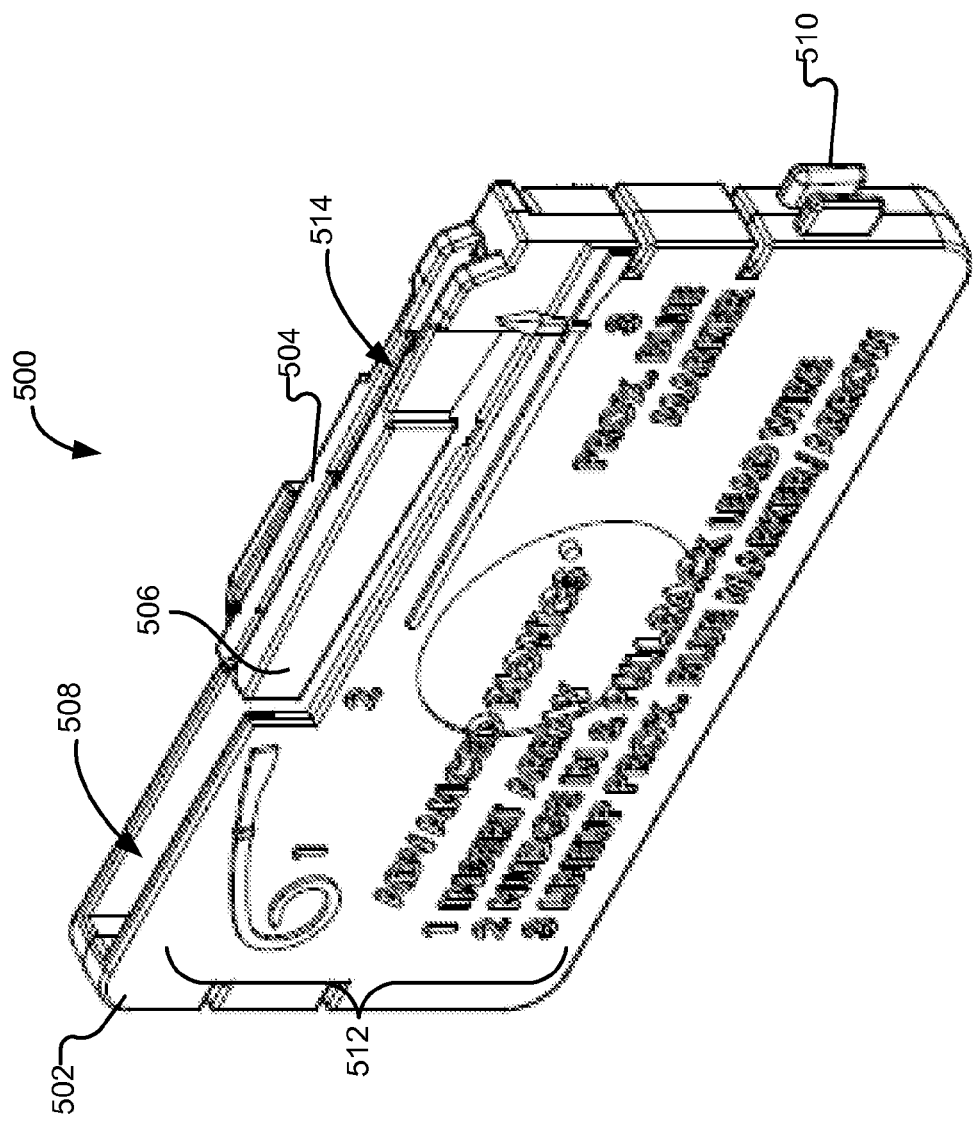
FIG. 5 is a perspective view of an exemplary loading tool according to principles described herein.

FIG. 5 illustrates an exemplary loading tool 500 for loading a pre-curved electrode array onto a straightening member according to principles described herein. As shown in FIG. 5, loading tool 500 may include a body 502, a first flexible arm 504, and a second flexible arm 506. In some examples, as will be explained in more detail below, first and second flexible arms 504 and 506 may each have a fixed end connected to body 502 and a free end opposite the fixed end. First flexible arm 504 and second flexible arm 506 may define a straightening channel 514 configured to constrain a pre-curved electrode array disposed therein in a straightened configuration. In certain examples, as will be described in more detail below, first flexible arm 504 and second flexible arm 506 may also be configured to temporarily flex away from each other to receive the pre-curved electrode array into straightening channel 514.

Body 502 may define a recess 508 configured to receive a curved portion of a pre-curved electrode array in a curved configuration. In some examples, the sides of body 502 may provide support to and may facilitate alignment of the electrode array within recess 508. In this manner, the electrode array may be properly aligned with straightening channel 514 when disposed within loading tool 500.

Body 502 may be of any suitable shape and/or size as may serve a particular application. For example, body 502 may be generally rectangular, as shown in FIG. 5. In some examples, body 502 may be dimensioned to facilitate convenient handling thereof by a surgeon or other user. For example, an alternative shape of body 502 than that shown in FIG. 5 may include a curved portion configured to rest on a user's index finger while the user utilizes loading tool 500.

As shown in FIG. 5, first flexible arm 504 and second flexible arm 506 may be adjacent to each other while in an un-flexed position or state. In certain examples, first flexible arm 504 and second flexible arm 506 may abut against each other. As will be described in more detail below, first flexible arm 504 and second flexible arm 506 may operate jointly to perform one or more functions of loading tool 500. For example, first flexible arm 504 and second flexible arm 506 may be configured to constrain a pre-curved electrode array within straightening channel 514 to facilitate insertion of a straightening member into the pre-curved electrode array.

Loading tool 500 may also include a gripping element 510 configured to hold a pre-curved electrode array in place as a straightening member is inserted into a portion of the pre-curved electrode array that is disposed in straightening channel 514. For example, gripping element 510 may include prongs extending from body 502 configured to grip opposite sides of a lead body (e.g., lead body 208) to prevent the lead body from interfering with the insertion of a straightening member into the electrode array. Additionally or alternatively, gripping element 510 may grip the lead in any other suitable manner (e.g., through a friction fit, an interference fit, a snap fit, etc.).

Body 502 may include instructions 512 disposed thereon to assist a user utilizing loading tool 500. For example, FIG. 6, which illustrates a side view of loading tool 500, shows that body 502 may include written instructions (e.g., written steps) and graphical indicia (e.g., position markers, direction indicators, etc.) instructing a user on how to utilize loading tool 500. To illustrate, instructions 512 include written instructions for a user to first "INSERT ARRAY," second "NUDGE IN & PULL BACK LEAD WIRE," and third "LINE UP PROX. BLUE MARKER/ARROW." In turn, the graphical indicia may correspond to the written instructions and may include graphical objects (e.g., representing an electrode array in a straightened or curved configuration), direction indicators, position markers (e.g., markers indicating where to line up a lead), and/or any other suitable graphical indicia. Instructions 512 are provided for exemplary purposes only. One will appreciate that instructions 512 may include any other written instructions, graphical indicia, and/or other symbols configured to provide instruction to a user on how to utilize loading tool 500. Additionally or alternatively, a lead configured to be utilized with loading tool 500 may include indicia (e.g., position markers) thereon corresponding to instructions 512 disposed on body 502. In some examples, instructions 512 may be integrally formed with body 502 (e.g., instructions 512 may include raised lettering and/or graphics molded onto body 502).

Figure 6:
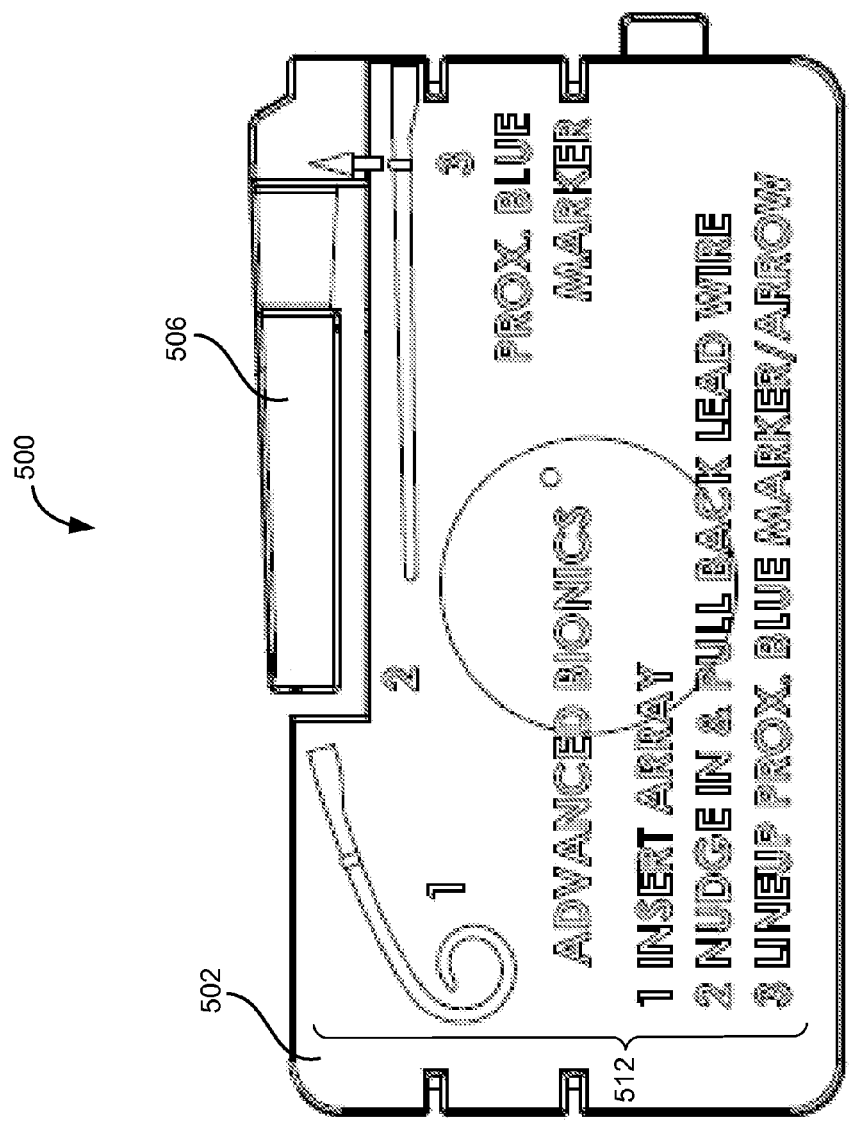
FIG. 6 is a side view of the exemplary loading tool of FIG. 5 according to principles described herein.

As also shown in FIG. 6, second flexible arm 506 may taper from a narrow distal end to a larger proximal end. For example, a bottom edge of second flexible arm 506 may be generally horizontal while an upper edge of second flexible arm 506 may angle upwards from a distal end (e.g., from the left) to a proximal end (e.g., to the right). This angled or tapered configuration may facilitate disposal of a pre-curved electrode array into straightening channel 514 and/or may prevent the inadvertent removal of the pre-curved electrode array from straightening channel 514. The size and shape of second flexible arm 506 are shown for illustrative purposes only. Second flexible arm 506 may have any other size and shape suitable for facilitating disposal of a pre-curved electrode array into straightening channel 514. Additionally or alternatively, first flexible arm 504 may have a size and shape that correspond to the size and shape of second flexible arm 506.

Figure 7:
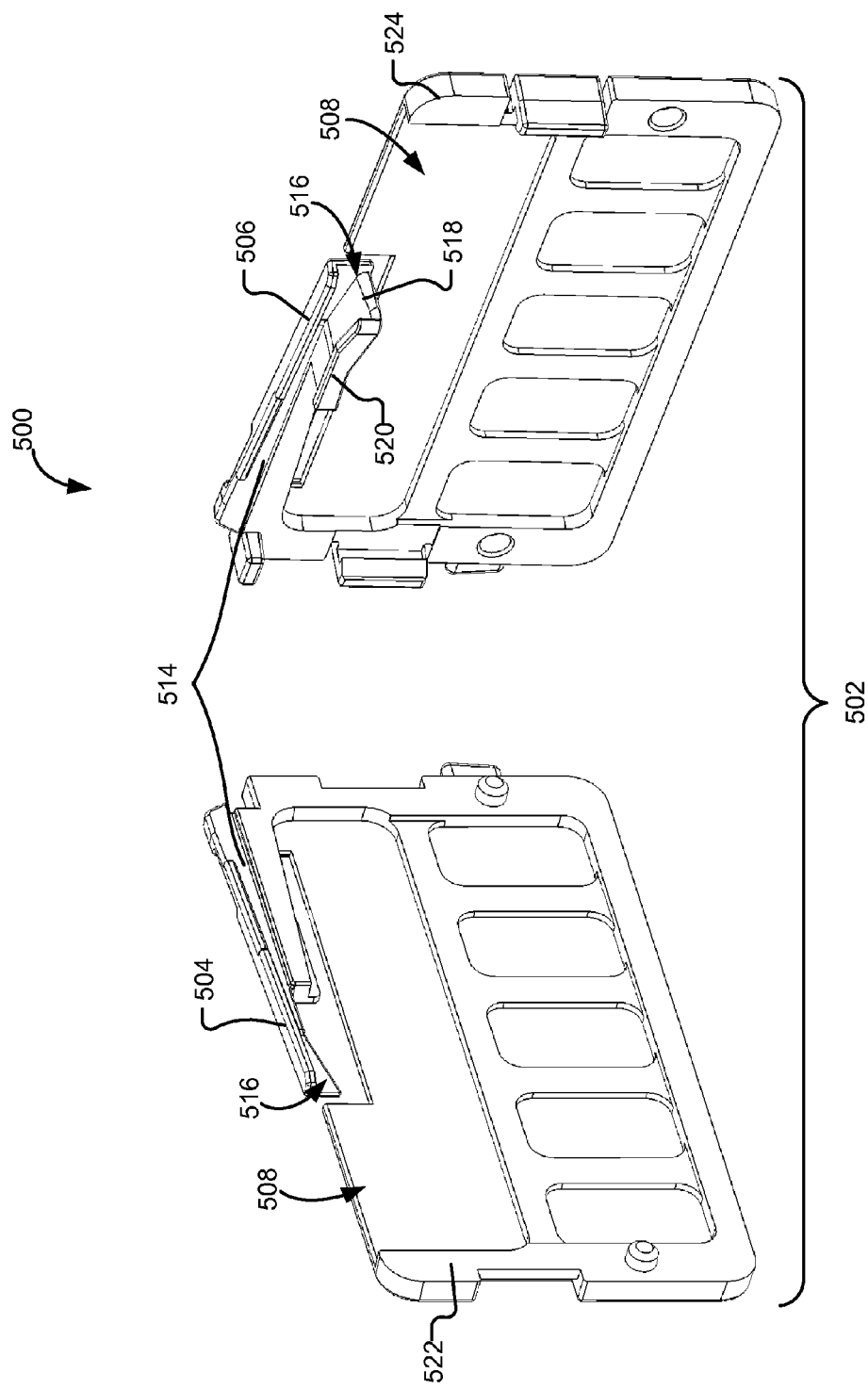
FIG. 7 is an exploded view of the exemplary loading tool of FIG. 5 according to principles described herein.

FIG. 7 illustrates an exploded view of loading tool 500. As shown in FIG. 7, body 502 may include a first side member 522 and a second side member 524 configured to be coupled together to form body 502. In certain examples, first side member 522 and second side member 524 may be configured to clip together. However, one will appreciate that first side member 522 and second side member 524 may couple together in any other suitable manner (e.g., by way of a snap fit, a friction fit, an interference fit, etc.).

As shown in FIG. 7, first side member 522 may be integrally formed with first flexible arm 504 and second side member 524 may be integrally formed with second flexible arm 506. Alternatively, first flexible arm 504 and second flexible arm 506 may be formed separately and then coupled to side members 522 and 524, respectively.

First flexible arm 504 and second flexible arm 506 may include corresponding features configured to jointly define straightening channel 514. In some examples, first flexible arm 504 and second flexible arm 506 may each define one or more surfaces of straightening channel 514. For example, each of first flexible arm 504 and second flexible arm 506 may define substantially half of straightening channel 514. Alternatively, one will appreciate that each of first flexible arm 504 and second flexible arm 506 may define more or less of straightening channel 514 as may serve a particular implementation.

Straightening channel 514 may be configured to constrain an electrode array in a straightened configuration. In some examples, straightening channel 514 may have a size and shape that corresponds to the size and shape of a straightened electrode array. For example, straightening channel 514 may have a tapered configuration corresponding to an electrode array that tapers from a larger proximal end to a smaller distal end. However, one will appreciate that straightening channel 514 may have any size, shape, and/or configuration suitable for constraining a pre-curved electrode array in a straightened configuration.

In some examples, the free ends of first flexible arm 504 and second flexible arm 506 may define a mouth 516 configured to receive a pre-curved electrode array and facilitate guiding of the pre-curved electrode array from a curved configuration while positioned in recess 508 into a straightened configuration while positioned in straightening channel 514. For example, mouth 516 may be configured to engage a pre-curved electrode array as it is pulled into straightening channel 514 to move the pre-curved electrode array from the curved configuration to a straightened configuration. In some examples, mouth 516 may have a flared opening to facilitate receiving and/or straightening the pre-curved electrode array.

As mentioned above, first flexible arm 504 and second flexible arm 506 may be configured to flex away from each other to facilitate positioning of an electrode array in straightening channel 514. To illustrate, first flexible arm 504 and second flexible arm 506 may flex from an adjacent position to a separated position to allow a user to insert a portion of a pre-curved electrode array into straightening channel 514, after which first flexible arm 504 and second flexible arm 506 may return to the non-flexed, adjacent positions. Additionally or alternatively, first flexible arm 504 and second flexible arm 506 may flex from an adjacent position to a separated position to allow a portion of pre-curved electrode array to be moved (e.g., pulled) into straightening channel 514, after which first flexible arm 504 and second flexible arm 506 may return to the adjacent position to constrain the electrode array within straightening channel 514. The flexibility of first flexible arm 504 and second flexible arm 506 may be adjusted as desired for a particular application. For example, a manufacturer may select any suitable material or combination of materials for first flexible arm 504 and second flexible arm 506 in order to achieve any desired amount of flexibility in first flexible arm 504 and second flexible arm 506.

Second flexible arm 506 may include a tab 518 configured to extend under first flexible arm 504. Tab 518 may interface with first flexible arm 504 and be configured to stabilize interaction between and align first flexible arm 504 and second flexible arm 506. In certain examples, tab 518 may include a lip 520 positioned at an end thereof and configured to prevent excessive separation between first flexible arm 504 and second flexible arm 506. For example, when assembled, lip 520 may be positioned opposite of first flexible arm 504 from second flexible arm 506 and may prevent excessive separation of first flexible arm 504 and second flexible arm 506 (e.g., by abutting against the opposite side of first flexible arm 504 after first and second flexible arms 504 and 506 have flexed away from one another by a predetermined amount).

To illustrate how loading tool 500 may be utilized, a user may first position a pre-curved electrode array (e.g., electrode array 112) in a curved configuration into recess 508. The user may then position a portion of the pre-curved electrode array (e.g., lead body 208) into straightening channel 514. This may be accomplished by pressing (e.g., with a forefinger) the portion of the pre-curved electrode array down between first flexible arm 504 and a second flexible arm 506. In response to the resultant downward force, first flexible arm 504 and second flexible arm 506 may temporarily flex away from each other to allow the pre-curved electrode array to be positioned within straightening channel 514. Additionally or alternatively, first flexible arm 504 and second flexible arm 506 may have beveled or rounded adjacent edges configured to facilitate insertion of the pre-curved electrode array between first flexible arm 504 and second flexible arm 506. Thereafter, the user may pull on the pre-curved electrode array to advance the pre-curved electrode array through mouth 516 and into straightening channel 514. As this is done, mouth 516 may engage and at least partially straighten the pre-curved electrode array as it moves into straightening channel 514. In addition, first flexible arm 504 and second flexible arm 506 may temporarily flex away from each other to facilitate entry of the electrode array into straightening channel 514. Thereafter, first flexible arm 504 and second flexible arm 506 may return to their non-flexed positions to constrain the electrode array in a straightened configuration within straightening channel 514.

While the electrode array is constrained within straightening channel 514 in a straightened configuration, a user may insert a straightening member into the electrode array to retain the electrode array in its straightened configuration after removal from loading tool 500. To facilitate insertion of the straightening member, a user may insert a portion of the electrode array that is not constrained within straightening channel 514 (e.g., lead body 208) into gripping element 510 to ensure that the unconstrained portion of the lead does not interfere with insertion of the straightening member. After the straightening member has been inserted into the electrode array, the electrode array and inserted straightening member may be removed from loading tool 500 (e.g., by pulling the electrode array out of straightening channel 514 and/or by separating first side member 522 and second side member 524). A surgeon may then insert the electrode array into a cochlea using the straightening member and/or any other tools (e.g., a forceps, an insertion tool, etc.).

Figure 8:
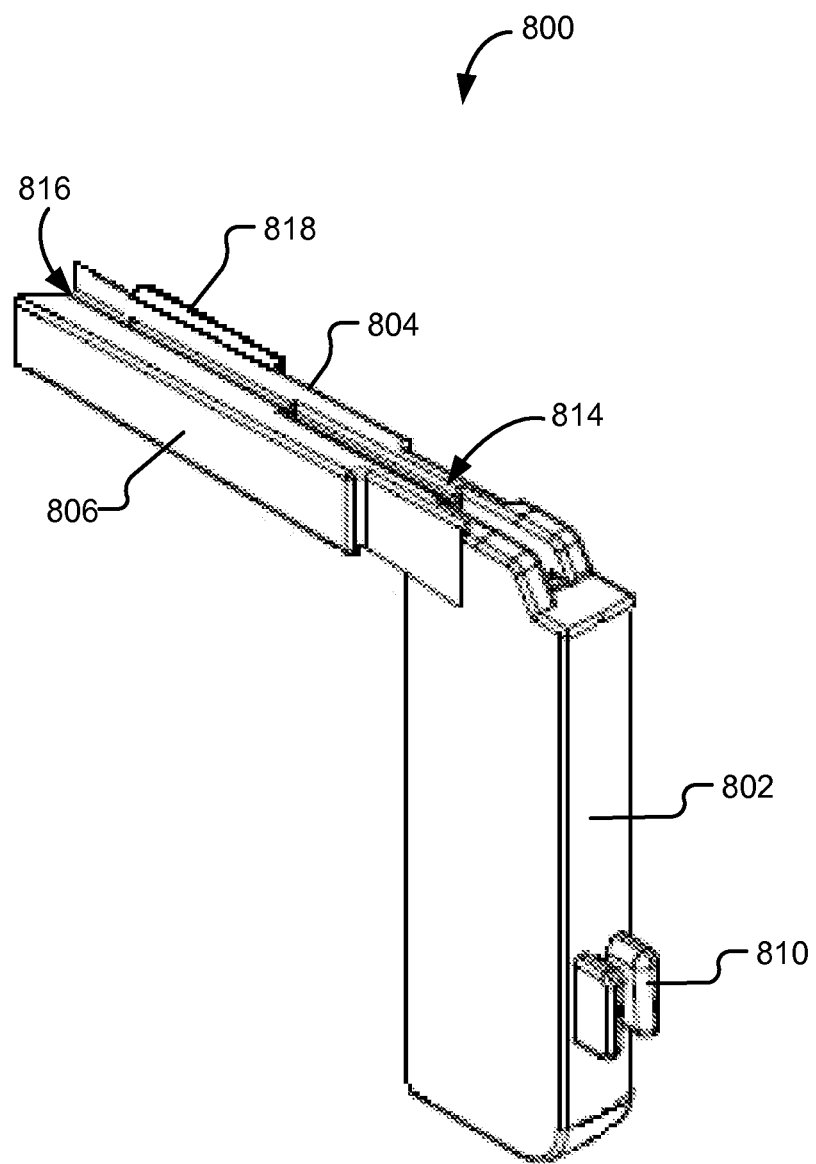
FIG. 8 illustrates an additional exemplary loading tool according to principles described herein.

Reference is now made to FIG. 8, which illustrates an additional exemplary loading tool 800 configured to facilitate loading of a pre-curved electrode array onto a straightening member according to principles described herein. Loading tool 800 may be similar in many respects to loading tool 500. Therefore, some elements of loading tool 800 may not be described herein as they are described in more detail above. In some examples, loading tool 800 may incorporate any of the elements of loading tool 500 as described in more detail above and shown in FIGS. 5-7, and/or of loading tool 1000 as described in more detail below and shown in FIGS. 10-11.

Loading tool 800 may include a body 802, a first flexible arm 804, and a second flexible arm 806. Loading tool 800 may be configured to straighten a pre-curved electrode array in order to facilitate insertion of a straightening member into the pre-curved electrode array. In some examples, first flexible arm 804 and second flexible arm 806 may be positioned adjacent to each other in an un-flexed state and define a straightening channel 814 configured to constrain a pre-curved electrode array in a straightened configuration. First flexible arm 804 and second flexible arm 806 may be configured to flex away from each other to facilitate movement of a pre-curved electrode array into straightening channel 814 and then return to their un-flexed positions to constrain the pre-curved electrode array within straightening channel 814.

First flexible arm 804 and second flexible arm 806 may also define a mouth 816 configured to receive a pre-curved electrode array and facilitate guiding the pre-curved electrode array from a curved configuration into a straightened configuration and into straightening channel 814. In certain examples, mouth 816 may include a flared opening to facilitate movement of the pre-curved electrode array into straightening channel 814.

Figure 9:
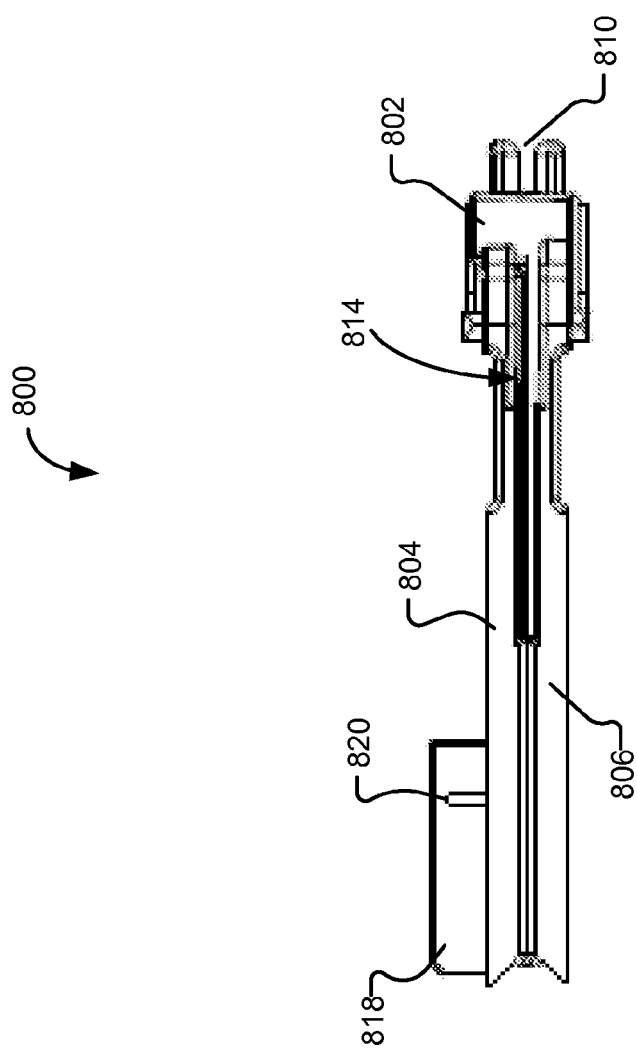
FIG. 9 is a top view of the exemplary loading tool of FIG. 8 according to principles described herein.

As shown in FIG. 9, which illustrates a top view of loading tool 800, second flexible arm 806 may include a tab 818 extending underneath first flexible arm 804. Tab 818 may be configured to align first flexible arm 804 and second flexible arm 806 and stabilize interaction between first flexible arm 804 and second flexible arm 806. In certain examples, tab 818 may be configured to limit relative movement between first flexible arm 804 and second flexible arm 806. As shown, tab 818 may define a groove 820 configured to interact with the first flexible arm 804. For example, first flexible arm 804 may include a projection member (e.g., a pin) extending at least partially into groove 820. The projection member may interact with groove 820 to limit and/or guide separation of first flexible arm 804 and second flexible arm 806.

Loading tool 800 may also include a gripping element 810 configured to grip and stabilize an unconstrained portion of a lead (e.g., lead body 208) to prevent the unconstrained portion from interfering with insertion of a straightening member into a straightened portion of the electrode array constrained within straightening channel 814. Loading tool 800 may be configured to operate similar to the operation of loading tool 500 as explained in more detail above and as will be explained in more detail below.

Figure 10:
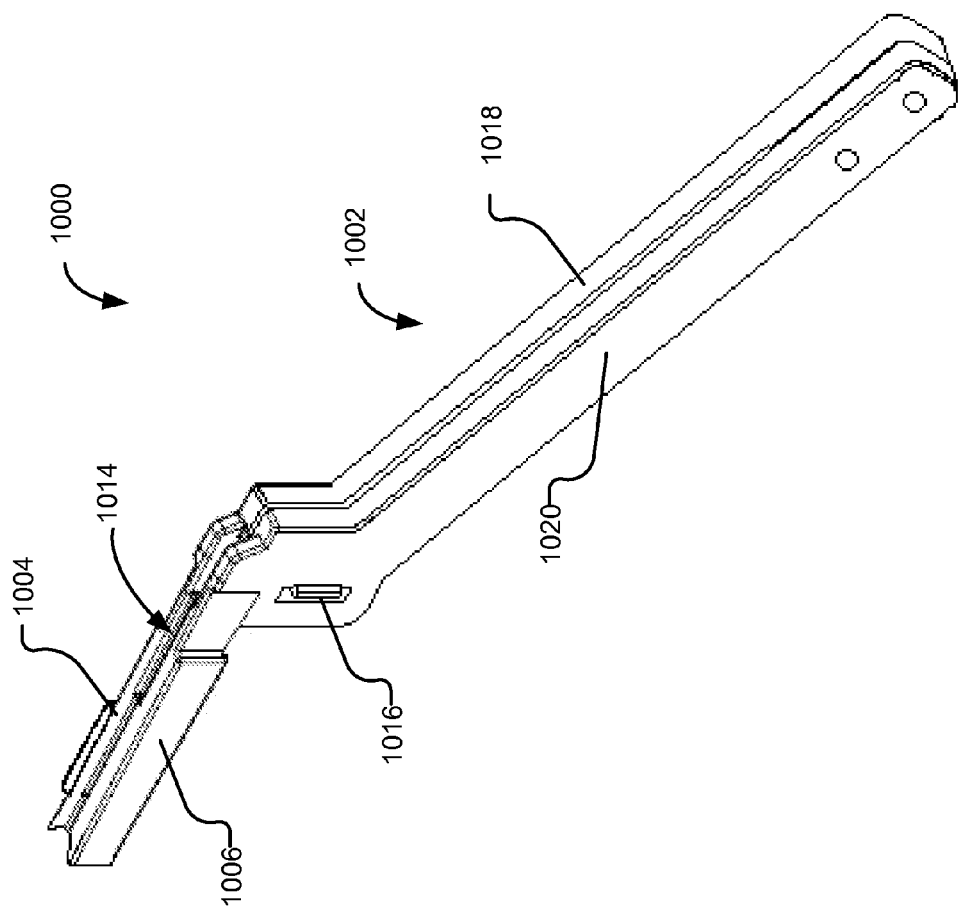
FIG. 10 illustrates another exemplary loading tool according to principles described herein.
Figure 11:
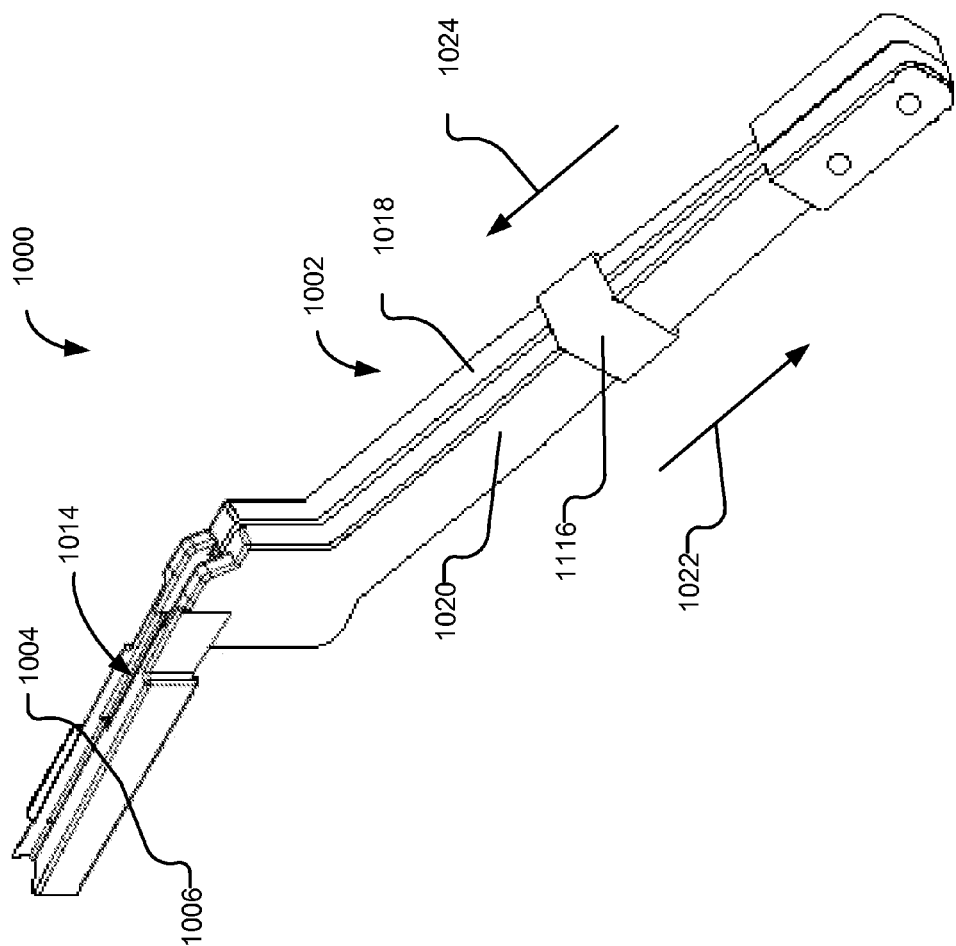
FIG. 11 illustrates an alternative example of the exemplary loading tool of FIG. 10 according to principles described herein.

Reference is now made to FIGS. 10-11, which illustrate an additional exemplary loading tool 1000 for loading a pre-curved electrode array onto a straightening member. As shown in FIGS. 10-11, loading tool 1000 may have a forceps-like configuration. Loading tool 1000 may be similar in many respects to loading tools 500 and 800 described in more detail above and shown in FIGS. 5-9. Accordingly, some elements of loading tool 1000 may not be described herein as they are described in more detail above. Additionally or alternatively, loading tool 1000 may incorporate any of the elements of loading tools 500 and 800 as may be suitable for a particular application.

As shown in FIG. 10, loading tool 1000 may include a body 1002, a first flexible arm 1004, and a second flexible arm 1006. First flexible arm 1004 and second flexible arm 1006 may define a straightening channel 1014 configured to constrain a pre-curved electrode array in a straightened configuration according to principles described herein.

In some examples, body 1002 may include a first side member 1018 integral with first flexible arm 1004 and a second side member 1020 integral with second flexible arm 1006. First side member 1018 and second side member 1020 may be coupled together at a proximal end and may be configured to selectively separate to facilitate insertion of a pre-curved electrode array into straightening channel 1014 and/or to facilitate removal of a straightened electrode array from straightening channel 1014. In some examples, first side member 1018 and second side member 1020 may be biased towards an opened, separated position. For example, when unconstrained, first side member 1018 and second side member 1020 may move to an opened position. A user (e.g., a physician) may overcome this bias by moving (e.g., by squeezing) the first side member 1018 and second side number 1020 together.

Loading tool 1000 may also include a locking mechanism configured to selectively lock first side member 1018 and second side number 1020 together in a closed position, as shown in FIG. 10. For example, the locking mechanism may comprise a ratchet lock 1016. In some examples, ratchet lock 1016 may extend from first side member 1018 and through second side member 1020. Ratchet lock 1016 may include one or more teeth configured to engage second side member 1020 to lock first side member 1018 and second side member 1020 together in a closed position.

In an alternative example, the locking mechanism may include a slide lock 1116, as shown in FIG. 11. In some examples, slide lock 1116 may extend around and may be slidable relative to first side member 1018 and second side member 1020. In certain examples, sliding slide lock 1116 in a proximal direction (indicated by arrow 1022) may allow first side member 1018 and second side member 1020 to separate from a closed position to an opened position. Sliding slide lock 1116 in a distal direction (indicated by arrow 1024) may lock first side member 1018 and second side member 1020 in a closed position. Additionally or alternatively, first side member 1018 and second side member 1020 may have a tapered configuration configured to interact with slide lock 1116, as shown in FIG. 11.

In additional or alternative examples, the locking mechanism may include any other suitable elements for selectively locking first side member 1018 and second side member 1020 together.

Loading tools 500, 800, and 1000 or any components thereof may be made of or otherwise include any suitable materials. In some examples, loading tools 500, 800, and 1000 may be made of one or more plastics (e.g., polymers), metals (e.g., stainless steel), other suitable materials, or combinations thereof. Additionally or alternatively, the materials of loading tools 500, 800, and 1000 may be substantially transparent to allow a user to see an electrode array within loading tools 500, 800, and 1000 and verify the position and/or configuration of the electrode array within the loading tools 500, 800, and 1000. As a result, the user can visually verify that the electrode array is in the proper position and/or configuration prior to straightening the electrode array or inserting a straightening member into the electrode array.

Loading tools 500, 800, and 1000 are provided for exemplary purposes only. One will appreciate that additional loading tools according to principles described herein may include additional elements or may exclude certain elements.

Figure 12:
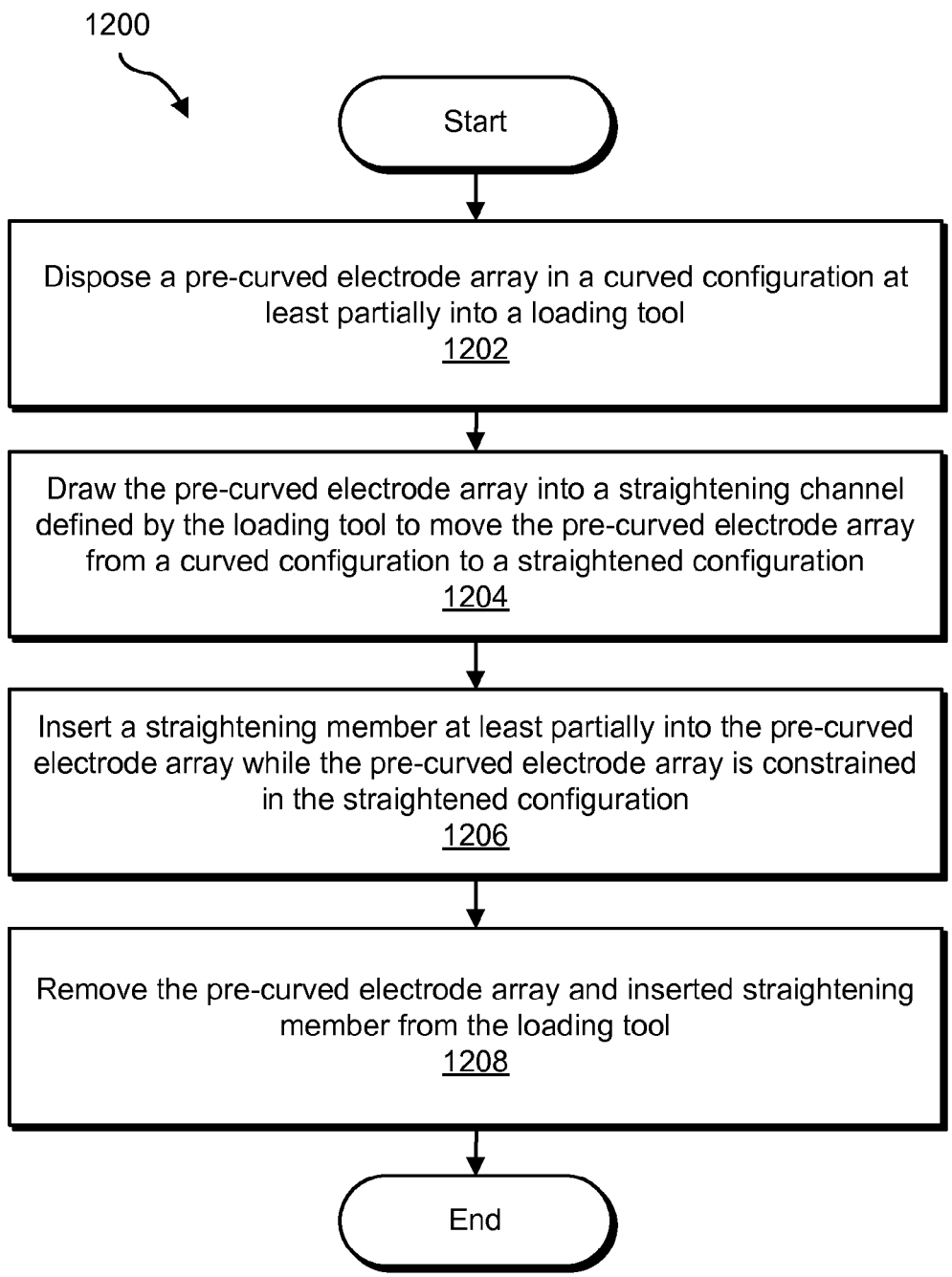
FIG. 12 illustrates an exemplary method of loading a pre-curved electrode array onto a straightening member according to principles described herein.

FIG. 12 illustrates an exemplary method 1200 of loading a pre-curved electrode array onto a straightening member using a loading tool (e.g., loading tool 500) according to principles described herein. While FIG. 12 illustrates exemplary steps according to one embodiment, other embodiments may omit, add to, reorder, and/or modify any of the steps shown in FIG. 12.

In step 1202, a pre-curved electrode array in a curved configuration is disposed at least partially into a loading tool. The loading tool may be similar to any loading tool (e.g., loading tool 500) disclosed herein. As described above, the loading tool may include a first flexible arm and a second flexible arm that define a straightening channel configured to constrain a pre-curved electrode array in a straightened configuration.

Figure 13A:
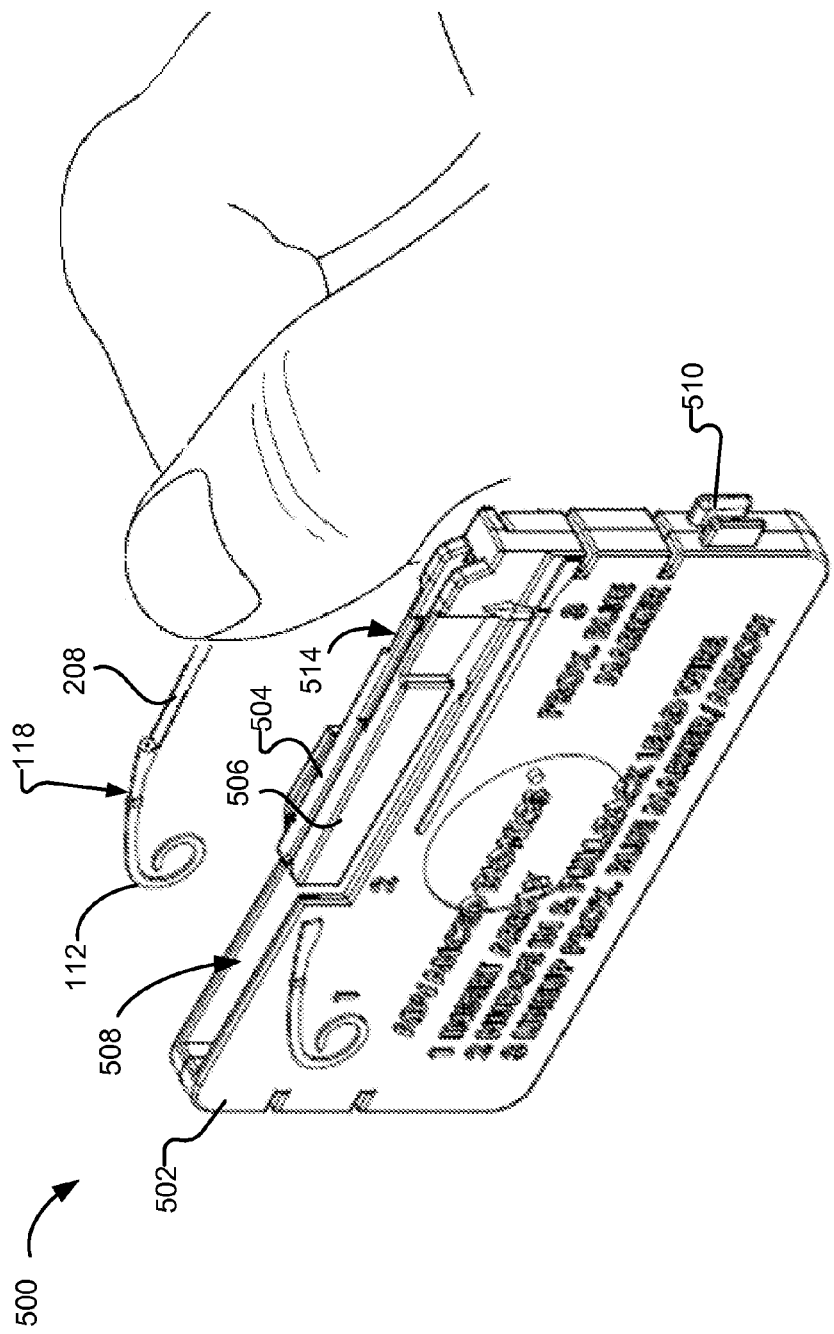
FIG. 13A illustrates a pre-curved electrode array being inserted into a recess of an exemplary loading tool according to principles described herein.
Figure 13B:
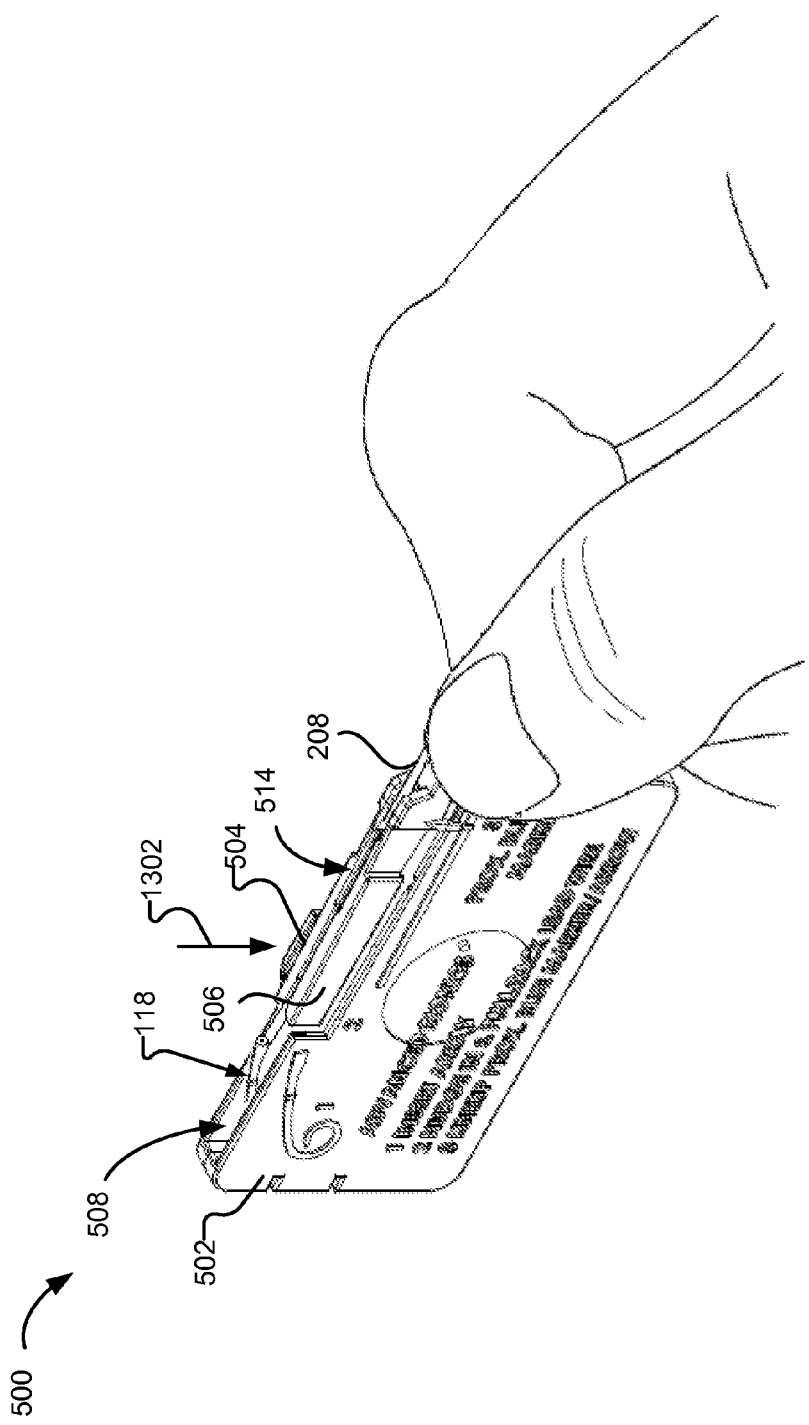
FIG. 13B illustrates a lead body of the pre-curved electrode array inserted into a straightening channel of the exemplary loading tool according to principles described herein.

To illustrate, FIG. 13A shows a lead 118 having a pre-curved electrode array 112 in a curved configuration ready to be positioned in loading tool 500. A surgeon or other user may place the curved portion of electrode array 112 within recess 508 and push lead body 208 in a direction indicated by arrow 1302 shown in FIG. 13B into straightening channel 514. FIG. 13B shows lead 118 after electrode array 112 has been placed within recess 508 and after lead body 208 has been disposed within straightening channel 514. As described in more detail above, first flexible arm 504 and second flexible arm 506 may temporarily flex away from each other to facilitate insertion of lead body 208 into straightening channel 514, after which first flexible arm 504 and second flexible arm 506 may return to their non-flexed position.

Figure 13C:
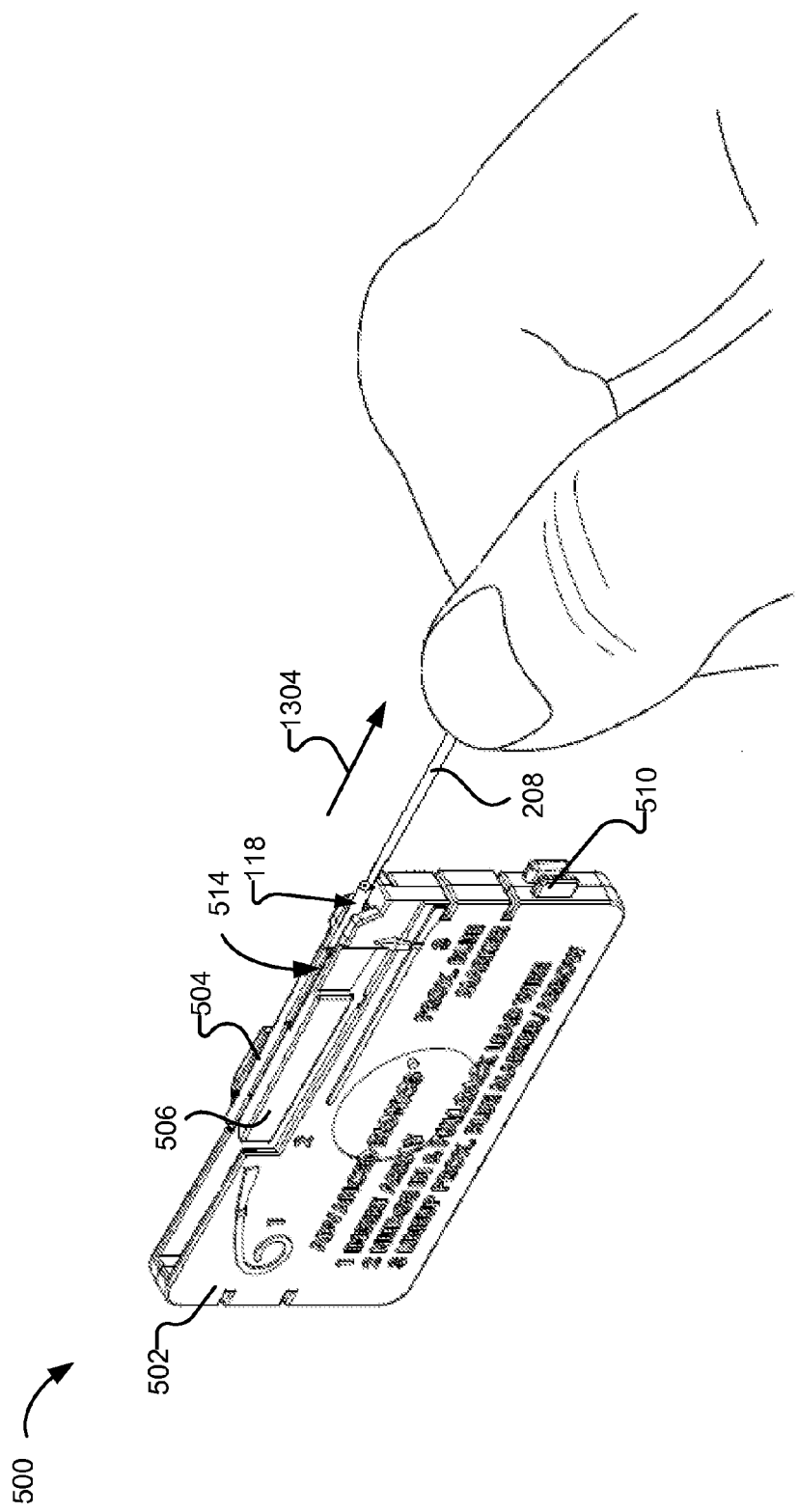
FIG. 13C illustrates a curved portion of the pre-curved electrode array being pulled into the straightening channel of the exemplary loading tool according to principles described herein.

In step 1204, the pre-curved electrode array is drawn into a straightening channel defined by the loading tool to move the pre-curved electrode array from a curved configuration to a straightened configuration. For example, FIG. 13C shows a lead body 208 of lead 118 being pulled in a proximal direction indicated by arrow 1304 to draw electrode array 112 into straightening channel 514 and move electrode array 112 from the curved configuration to a straightened configuration. As described in more detail above, first flexible arm 504 and second flexible arm 506 may temporarily flex away from each other to facilitate entry of electrode array 112 into straightening channel 514. Thereafter, first flexible arm 504 and second flexible arm 506 may return to their non-flexed position to constrain electrode array 112 within straightening channel 514.

Figure 13D:
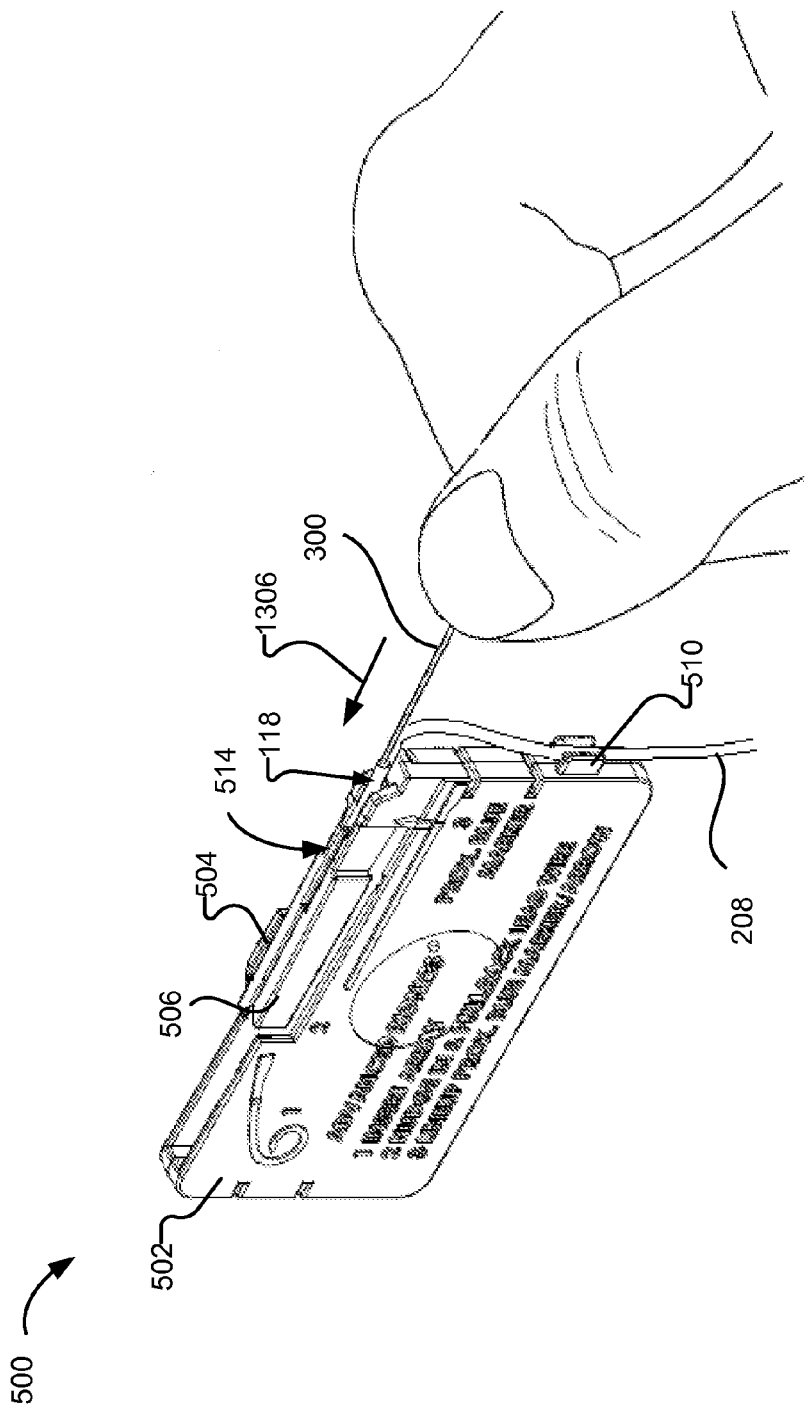
FIG. 13D illustrates a straightening member being inserted into the pre-curved electrode array according to principles described herein.

In step 1206, a straightening member is inserted at least partially into the pre-curved electrode array while the pre-curved electrode array is constrained in the straightened configuration. For example, FIG. 13D shows straightening member 300 being inserted into electrode array 112 (e.g., by pushing straightening member 300 in a direction indicated by arrow 1306 while electrode array 112 is constrained within straightening channel 514 in a straightened configuration. By moving the electrode array 112 to the straightened configuration prior to inserting straightening member 300, a user may avoid unnecessarily damaging electrode array 112 during insertion of straightening member 300. To prevent interference by lead body 208, lead body 208 may be temporarily retained by gripping element 510, as shown in FIG. 13D. Any other tools configured to facilitate proper insertion of straightening member 300 into electrode array 112 may be used as may serve a particular application.

Figure 13E:
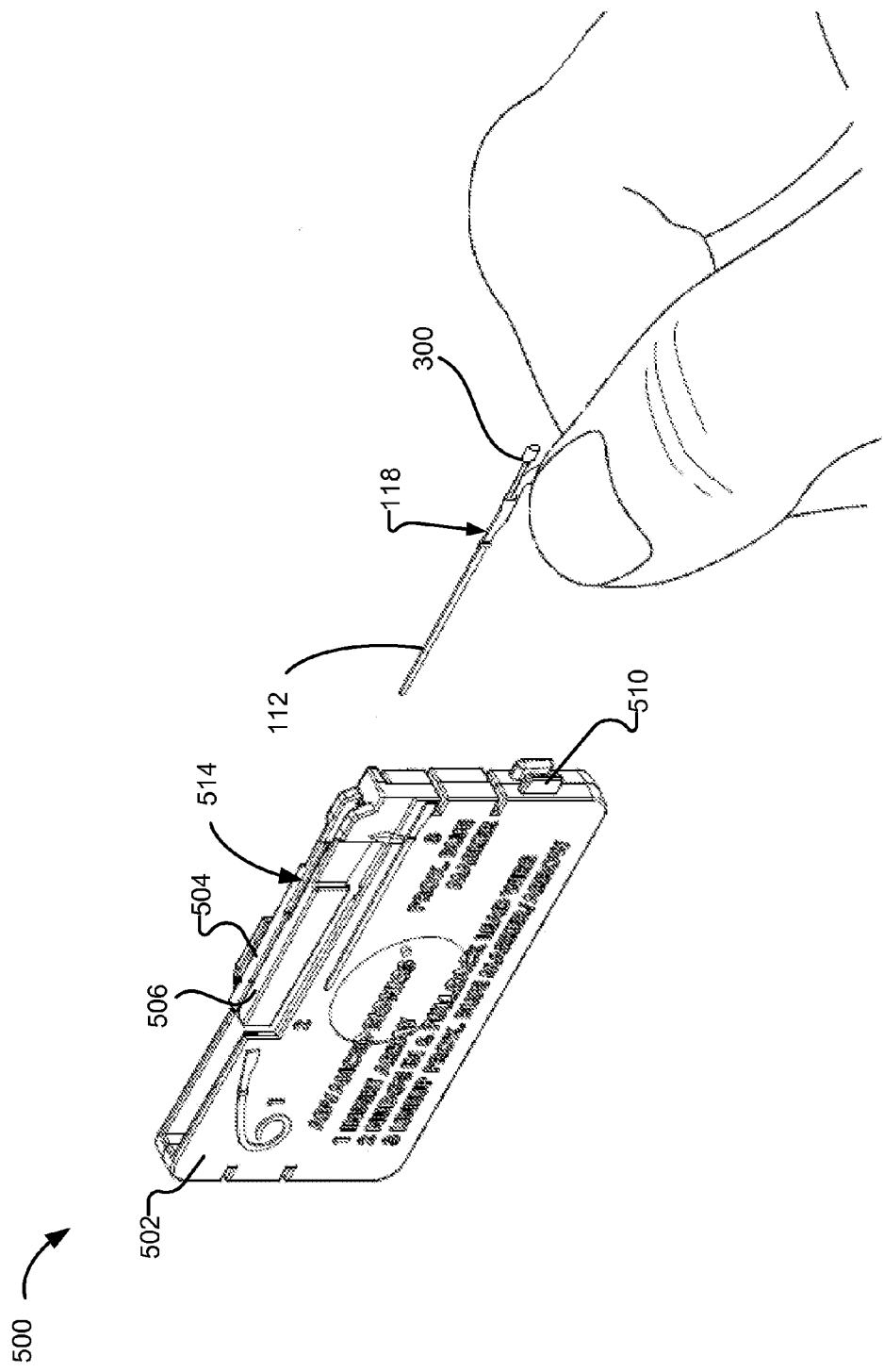
FIG. 13E illustrates the pre-curved electrode array and inserted straightening member being removed from the exemplary loading tool according to principles described herein.

In step 1208, the pre-curved electrode array and inserted straightening member are removed from the loading tool. For example, FIG. 13E shows electrode array 112 and inserted straightening member 300 being removed (e.g., by being pulled) from loading tool 500.

The steps illustrated in FIG. 12 may be performed to initially load a pre-curved electrode array onto a straightening member prior to a medical procedure in which a surgeon or other user attempts to insert the pre-curved electrode array into the cochlea of a patient. The steps illustrated in FIG. 12 may additionally or alternatively be used to reload the pre-curved array onto the straightening member during the medical procedure and/or at any other time as may serve a particular implementation. In this manner, the surgeon or other user may easily reload the pre-curved electrode array onto the straightening member after a failed attempt to insert the pre-curved electrode array into the cochlea.

In some examples, pre-curved electrode array 112 may be inserted into a duct of the cochlea in accordance with an off straightening member insertion technique. As used herein, an "off straightening member insertion technique" comprises any technique used to insert pre-curved electrode array 112 into a duct of the cochlea that, at least during a portion of the insertion process, does not employ the use of an insertion tool coupled to straightening member 300. For example, only the straightening member 300 may be used to initially insert pre-curved electrode array 112 at least partially into the cochlea. At some point, forceps or some other tool may be used to advance the pre-curved electrode array 112 all the way into the cochlea while holding straightening member 300 in a stationary position with respect to the cochlea. It will be recognized that other off straightening member insertion techniques may be used in accordance with the systems and methods described herein. It will also be recognized that any other insertion technique other than an off straightening member insertion technique may be used in accordance with the systems and methods described herein.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A system for loading a lead comprising a pre-curved electrode array onto a straightening member, the system comprising:
   a loading tool comprising
      a body,
      a first flexible arm having a fixed end connected to the body and a free end opposite the fixed end, and
      a second flexible arm having a fixed end connected to the body and a free end opposite the fixed end, wherein
         the first flexible arm and the second flexible arm define a straightening channel, and
         the first flexible arm and the second flexible arm flex away from each other to receive the pre-curved electrode array into the straightening channel and return from being flexed away from each other to a non-flexed position after the pre-curved electrode array is positioned within the straightening channel to constrain the pre-curved electrode array in a straightened configuration within the straightening channel; and
   a straightening member configured to be inserted into the pre-curved electrode array while the pre-curved electrode array is constrained in the straightened configuration and retain the pre-curved electrode array in the straightened configuration after the pre-curved electrode array is removed from the loading tool.

2. The system of claim 1, wherein the first flexible arm and the second flexible arm define a mouth configured to receive and straighten the pre-curved electrode array as it moves into the straightening channel.

3. The system of claim 2, wherein the mouth has a flared opening.

4. The system of claim 1, wherein the pre-curved electrode array has a shape that tapers from a proximal end to a distal end and wherein the straightening channel has a tapered configuration corresponding to the tapered shape of the pre-curved electrode array.

5. The system of claim 1, wherein the body defines a recess configured to receive the pre-curved electrode array in a curved configuration prior to the pre-curved electrode array being drawn into the straightening channel to move the pre-curved electrode array to the straightened configuration.

6. The system of claim 1, wherein the body comprises a first side member and a second side member configured to be coupled together.

7. The system of claim 6, wherein the first side member is integrally formed with the first flexible arm and the second side member is integrally formed with the second flexible arm.

8. The system of claim 7, wherein the loading tool has a forceps-like configuration.

9. The system of claim 8, wherein the loading tool further comprises a locking mechanism configured to selectively lock the first side member and the second side member in a closed position.

10. The system of claim 1, wherein the body further comprises instructions disposed thereon and configured to direct a user on how to utilize the loading tool, wherein the instructions include at least one of written instructions and graphical indicia.

11. The system of claim 1, further comprising a pre-curved electrode array.

12. A method of loading a lead comprising a pre-curved electrode array onto a straightening member, said method comprising:
    disposing the pre-curved electrode array in a curved configuration at least partially into a loading tool, the loading tool comprising:
        a body,
        a first flexible arm having a fixed end connected to the body and a free end opposite the fixed end, and
        a second flexible arm having a fixed end connected to the body and a free end opposite the fixed end, wherein
            the first flexible arm and the second flexible arm define a straightening channel, and
            the first flexible arm and the second flexible arm flex away from each other to receive the pre-curved electrode array into the straightening channel and return from being flexed away from each other to a non-flexed position after the pre-curved electrode array is positioned within the straightening channel to constrain the pre-curved electrode array in a straightened configuration within the straightening channel;
    drawing the pre-curved electrode array into the straightening channel of the loading tool to move the pre-curved electrode array from the curved configuration to the straightened configuration; and
    inserting a straightening member at least partially into the pre-curved electrode array while the pre-curved electrode array is constrained in the straightened configuration to retain the pre-curved electrode array in the straightened configuration.

13. The method of claim 12, further comprising removing the pre-curved electrode array and the inserted straightening member from the loading tool.

14. The method of claim 12, further comprising pushing a lead body of the pre-curved electrode array into the straightening channel and wherein the drawing of the pre-curved electrode array into the straightening channel comprises pulling the lead body until the pre-curved electrode array is positioned within the straightening channel in a straightened configuration.

15. A tool for loading a lead comprising a pre-curved electrode array onto a straightening member, the tool comprising:
    a body;
    a first flexible arm having a fixed end connected to the body and a free end opposite the fixed end; and
    a second flexible arm having a fixed end connected to the body and a free end opposite the fixed end; wherein
        the first flexible arm and the second flexible arm define a straightening channel, and
        the first flexible arm and the second flexible arm to separate to receive the pre-curved electrode array into the straightening channel and then return from being separated from each other to a non-flexed position after the pre-curved electrode array is positioned within the straightening channel to constrain the pre-curved electrode array in a straightened configuration within the straightening channel.

16. The tool of claim 15, wherein the first flexible arm and the second flexible arm define a mouth having a flared opening, the mouth configured to receive and straighten the pre-curved electrode array as it moves into the straightening channel.

17. The tool of claim 15, wherein the straightening channel has a tapered configuration corresponding to a tapered shape of the pre-curved electrode array.

18. The tool of claim 15, wherein the body comprises a first side member and a second side member, wherein the first side member and the second side member are configured to be coupled together, and wherein the first side member is integrally formed with the first flexible arm and the second side member is integrally formed with the second flexible arm.

19. The tool of claim 15, wherein the body further comprises instructions disposed thereon configured to direct a user on how to utilize the loading tool, wherein the instructions include at least one of written instructions and graphical indicia.

* * * * *